United States Patent
Suenaga et al.

(10) Patent No.: US 10,077,124 B2
(45) Date of Patent: Sep. 18, 2018

(54) BUBBLE REMOVAL METHOD AND BUBBLE REMOVAL DEVICE

(71) Applicant: TOYO SEIKAN GROUP HOLDINGS, LTD., Tokyo (JP)

(72) Inventors: Ryo Suenaga, Yokohama (JP); Satoshi Tanaka, Kanagawa (JP); Kyohei Ota, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 656 days.

(21) Appl. No.: 14/667,179

(22) Filed: Mar. 24, 2015

(65) Prior Publication Data

US 2015/0191262 A1 Jul. 9, 2015

Related U.S. Application Data

(63) Continuation of application No. PCT/JP2013/005226, filed on Sep. 4, 2013.

(30) Foreign Application Priority Data

Sep. 24, 2012 (JP) .................. 2012-209956

(51) Int. Cl.
| | |
|---|---|
| *B01D 19/00* | (2006.01) |
| *B65B 9/04* | (2006.01) |
| *B01L 3/00* | (2006.01) |
| *C12M 1/00* | (2006.01) |
| *C12M 1/34* | (2006.01) |
| *B65B 31/00* | (2006.01) |

(52) U.S. Cl.
CPC .............. *B65B 9/042* (2013.01); *B01L 3/505* (2013.01); *B65B 31/00* (2013.01); *C12M 23/14* (2013.01); *C12M 41/36* (2013.01); *B01L 3/502723* (2013.01); *B01L 2200/0684* (2013.01); *B01L 2300/0654* (2013.01); *B01L 2400/0481* (2013.01)

(58) Field of Classification Search
None
See application file for complete search history.

(56) References Cited

U.S. PATENT DOCUMENTS

| | | | |
|---|---|---|---|
| 5,985,653 A | 11/1999 | Armstrong et al. | |
| 5,994,129 A | 11/1999 | Armstrong et al. | |
| 6,096,532 A | 8/2000 | Armstrong et al. | |
| 6,228,635 B1 | 5/2001 | Armstrong et al. | |

(Continued)

FOREIGN PATENT DOCUMENTS

| | | |
|---|---|---|
| CN | 101157277 A | 4/2008 |
| EP | 1616619 A1 | 1/2006 |

(Continued)

OTHER PUBLICATIONS

Office Action in corresponding Korean Patent Application No. 10-2015-7003864 dated May 20, 2016, with translation (10 pages).

(Continued)

*Primary Examiner* — Amber Rose Orlando
*Assistant Examiner* — Phillip Y Shao
(74) *Attorney, Agent, or Firm* — Osha Liang LLP

(57) ABSTRACT

A method for removing bubbles from an observation area includes pressing, with a pressing member, a part of an upper surface of the container that is positioned above the observation area, and moving the pressing member so as to push the bubbles outside the observation area.

10 Claims, 13 Drawing Sheets

(56) References Cited

U.S. PATENT DOCUMENTS

| | | |
|---|---|---|
| 6,238,908 B1 | 5/2001 | Armstrong et al. |
| 2007/0037276 A1 | 2/2007 | De Crecy |
| 2008/0220501 A1 | 9/2008 | De Crecy |
| 2009/0233351 A1 | 9/2009 | Akechi |
| 2010/0120136 A1 | 5/2010 | Larsen et al. |
| 2012/0184009 A1 | 7/2012 | De Crecy |
| 2013/0143307 A1 | 6/2013 | Nozaki et al. |

FOREIGN PATENT DOCUMENTS

| | | |
|---|---|---|
| JP | H11-507229 A | 6/1999 |
| JP | 2004-198356 A | 7/2004 |
| JP | 2005034020 A | 2/2005 |
| JP | 2006314276 A | 11/2006 |
| JP | 2007197053 A | 8/2007 |
| JP | 2007522825 A | 8/2007 |
| JP | 2009031173 A | 2/2009 |
| JP | 2009521907 A | 6/2009 |
| JP | 2011-087498 A | 5/2011 |
| JP | 2012239401 A | 12/2012 |
| WO | 2007077607 A1 | 7/2007 |
| WO | 2012020458 A1 | 2/2012 |

OTHER PUBLICATIONS

Extended European Search Report dated Apr. 4, 2016, in corresponding European Patent Application No. 13839006.7 (6 pages).

Office Action dated Dec. 11, 2015, by the State Intellectual Property Office of The People's Republic of China in related Chinese Patent Application No. CN 201380047084.8, with English translation (9 pages).

Page 1022 of an article or book published Feb. 28 2001 (1 page).

Kanazawa, E. et al., Construction of Cell Culture Device Using Metal Modified Ceramics Carrier, Fukuoka Insdustrial Technology Center Kenkyu Hokoku, 2009, No. 19, pp. 58-61.

International Search Report and Written Opinon issued in corresponding International Application No. PCT/JP2013/005226 dated Nov. 26, 2013 (10 pages).

International Preliminary Report on Patentability issued in corresponding International Application No. PCT/JP2013/005226 dated Apr. 2, 2015 (2 pages).

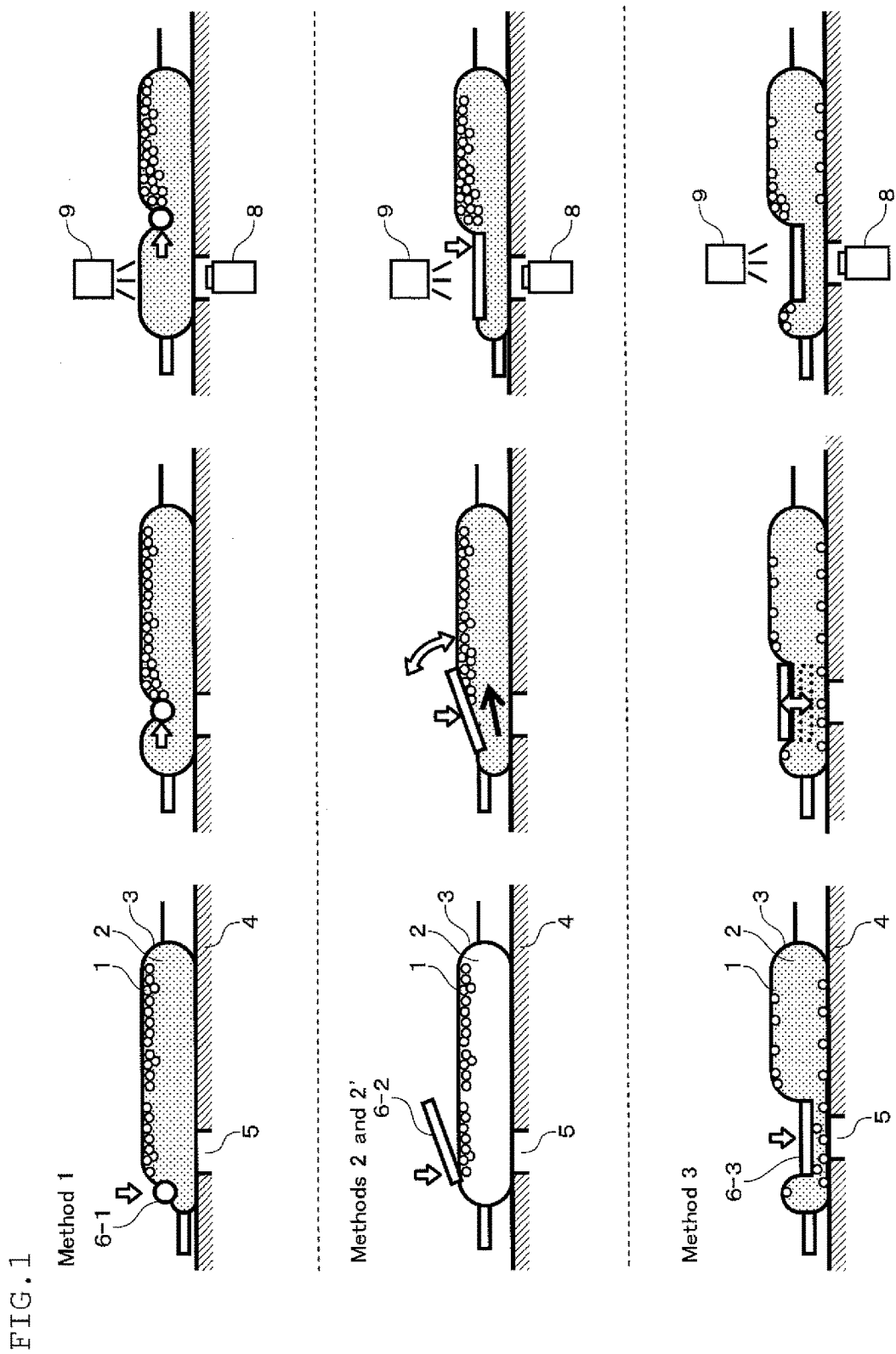

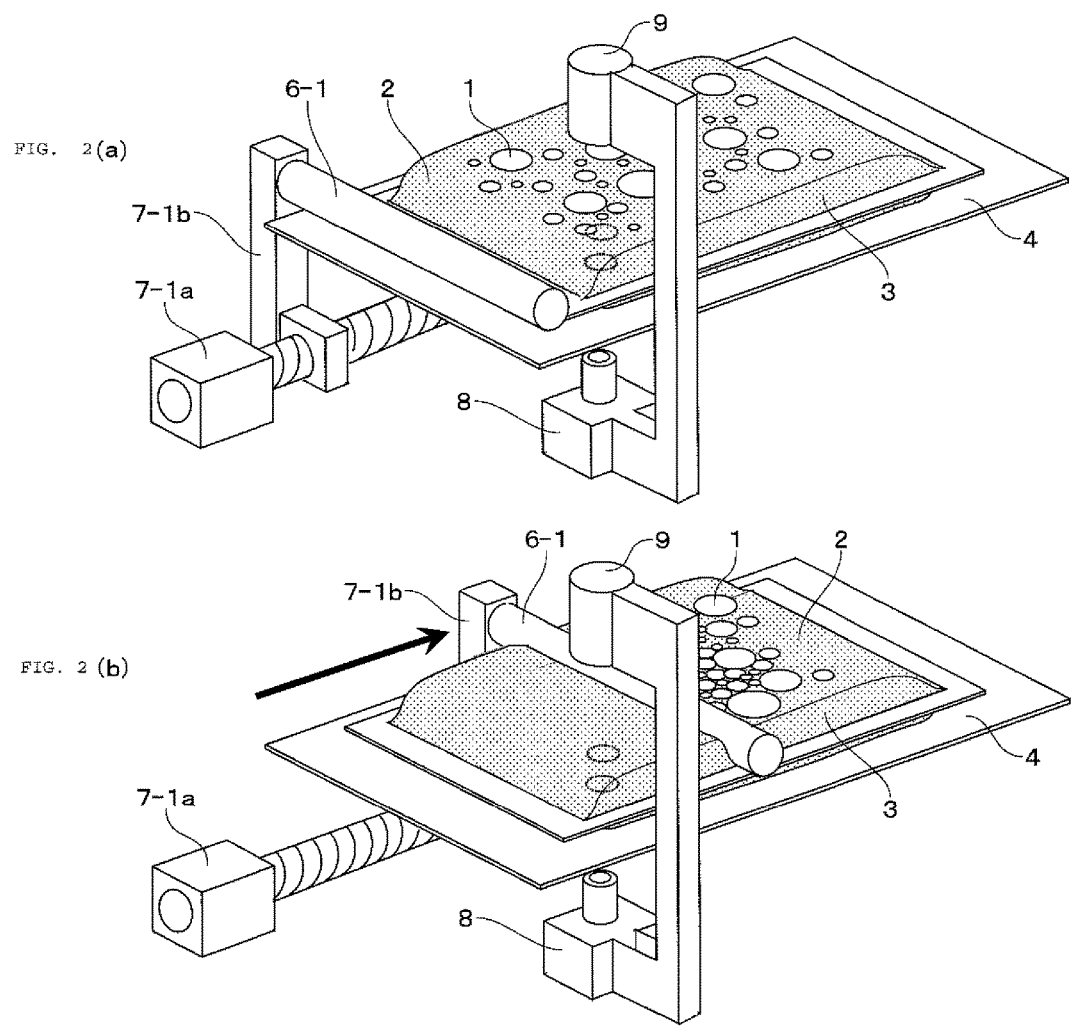

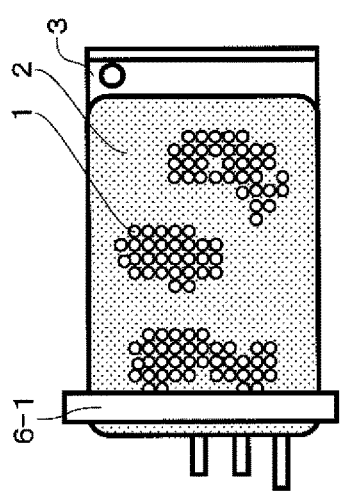
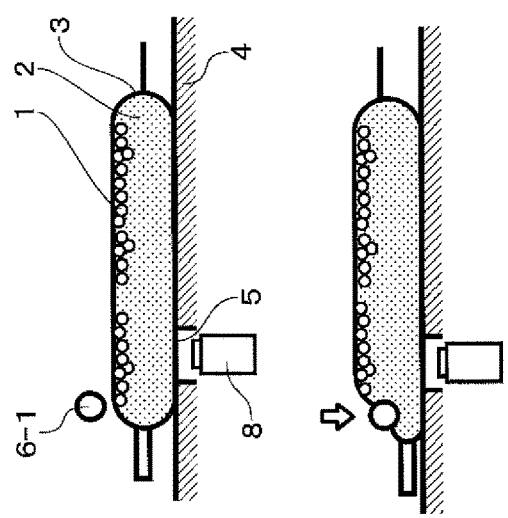
FIG. 3(a)
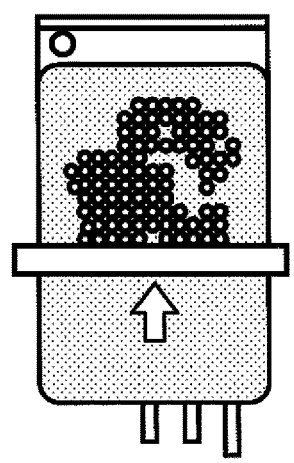
FIG. 3(b)
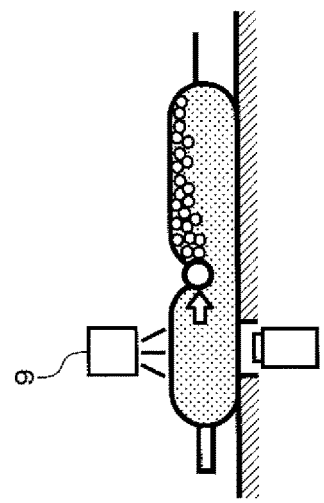
FIG. 3(c)

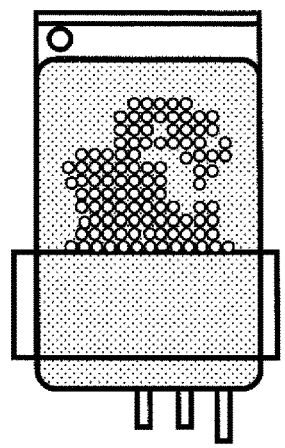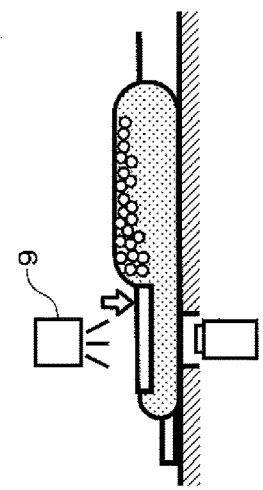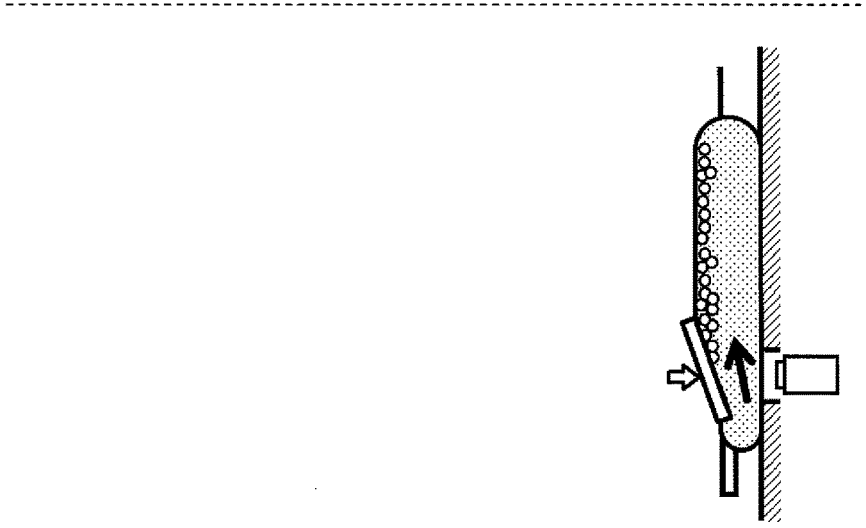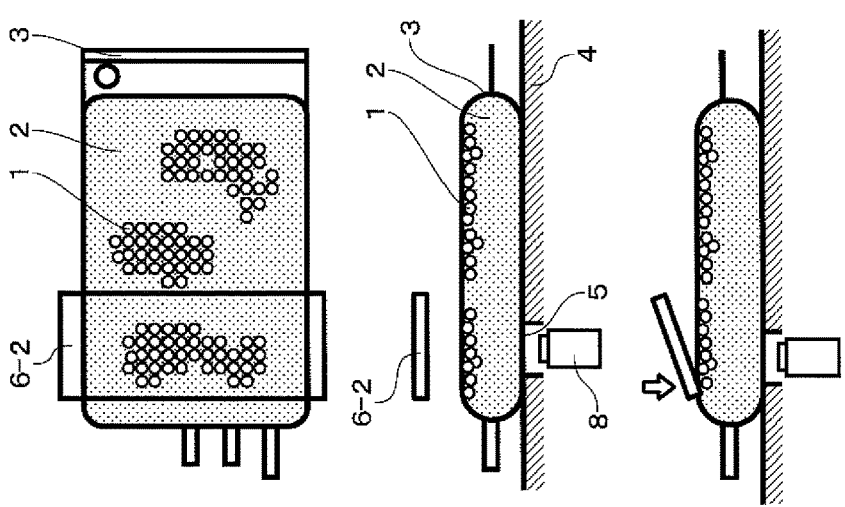
FIG. 5(a)  FIG. 5(b)  FIG. 5(c)

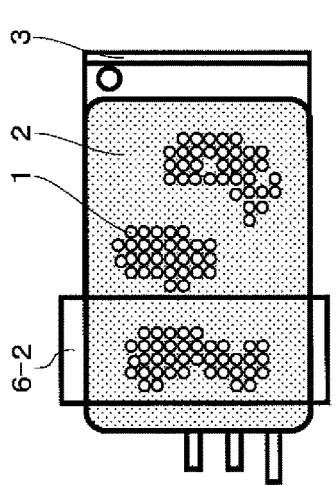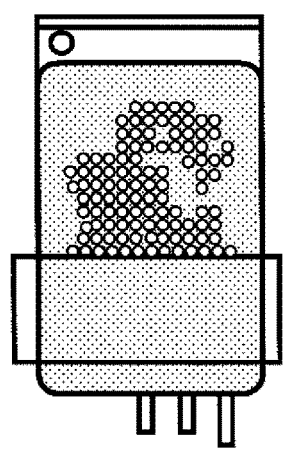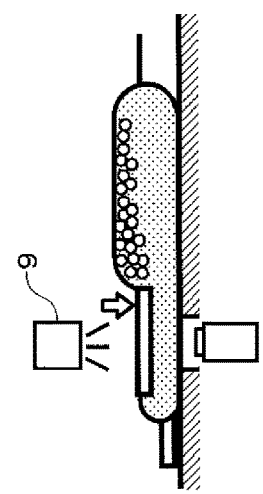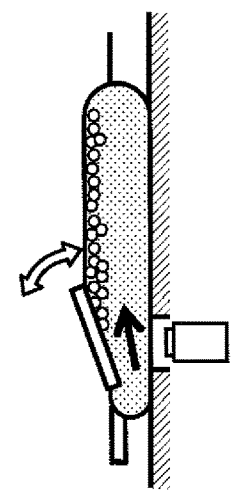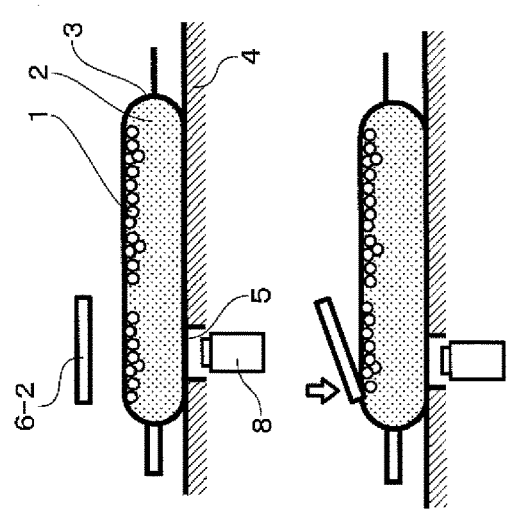
FIG. 6(a)  FIG. 6(b)  FIG. 6(c)

FIG. 8
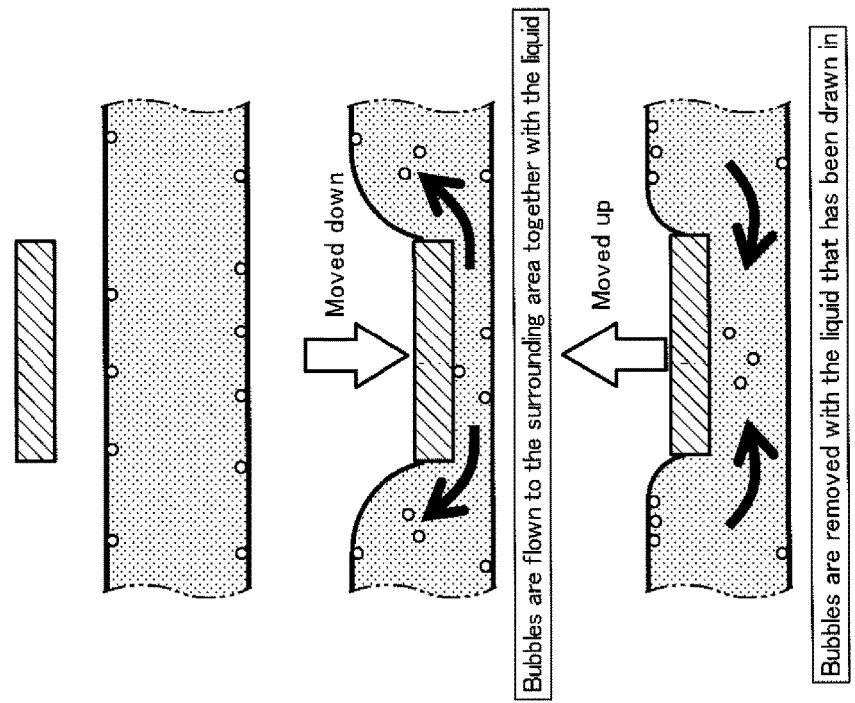
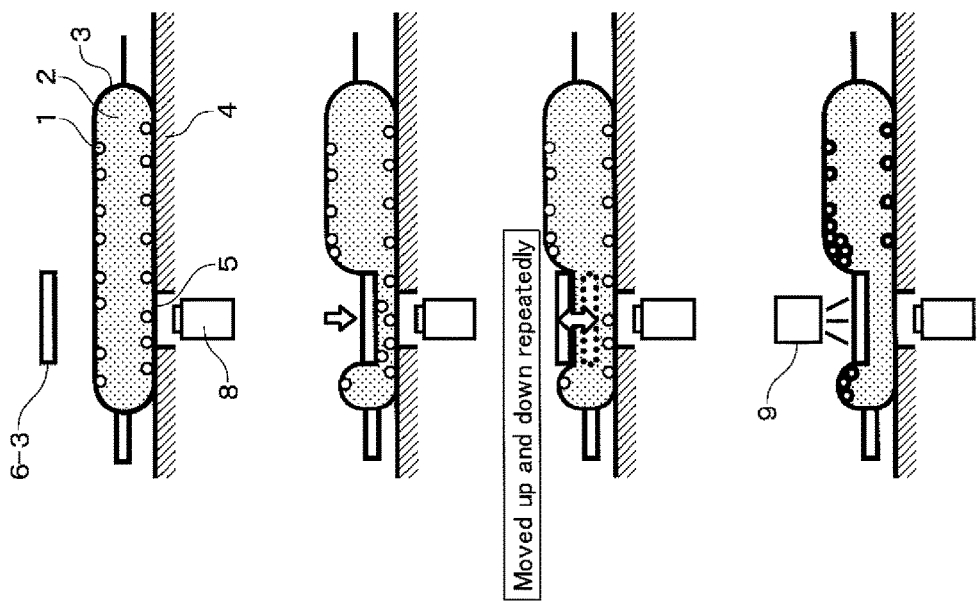

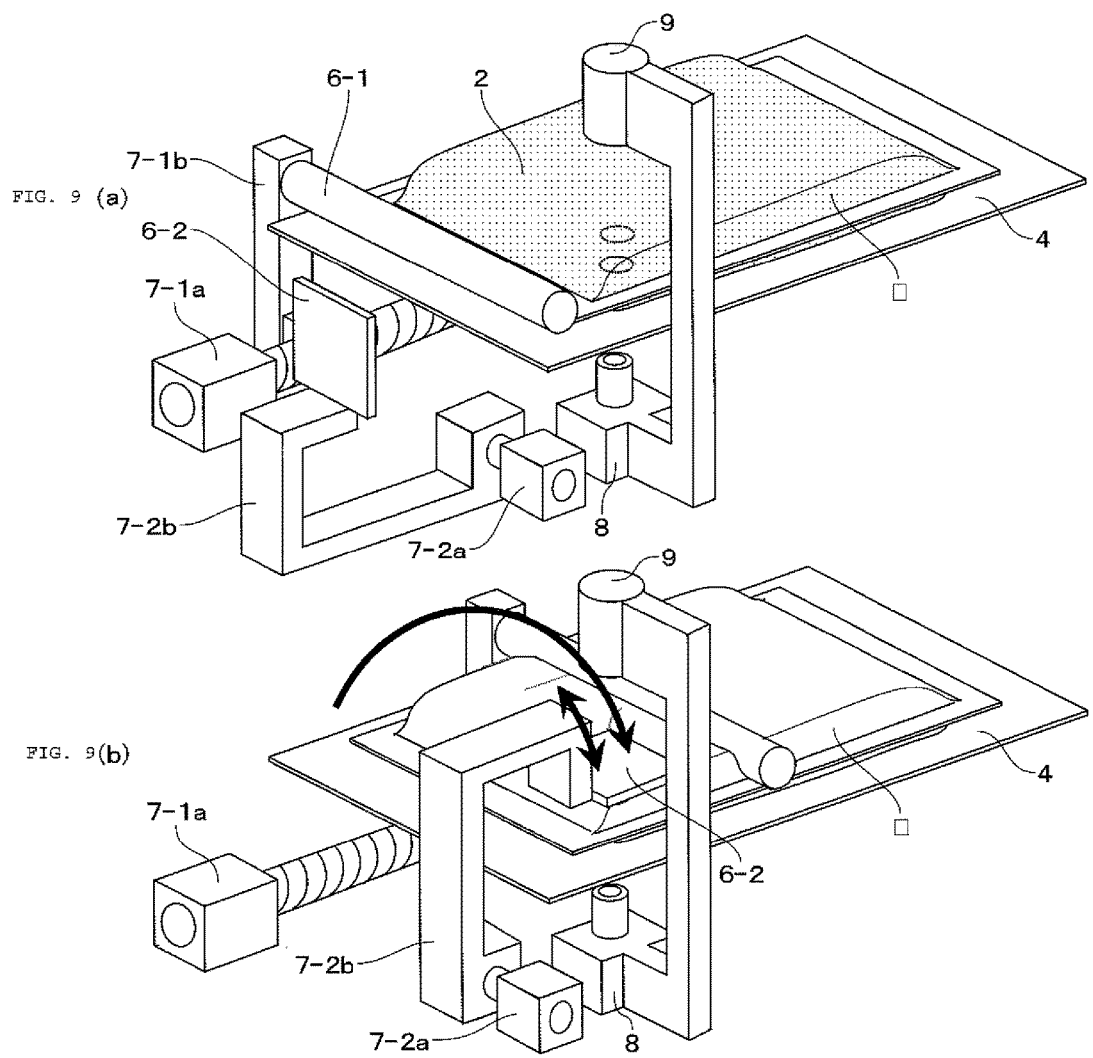

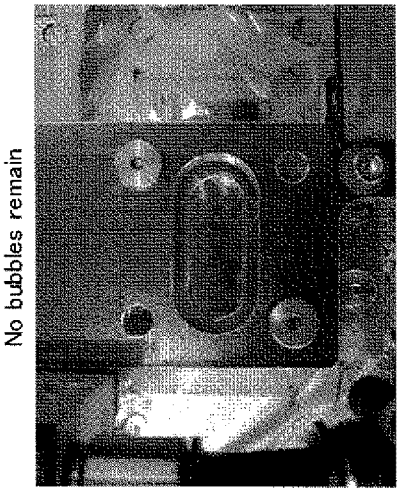
FIG. 11 (e) Second (down, up, down, up, down) No bubbles remain
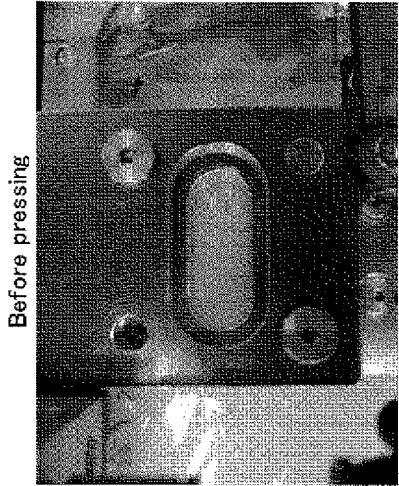
FIG. 11 (b) Before pressing
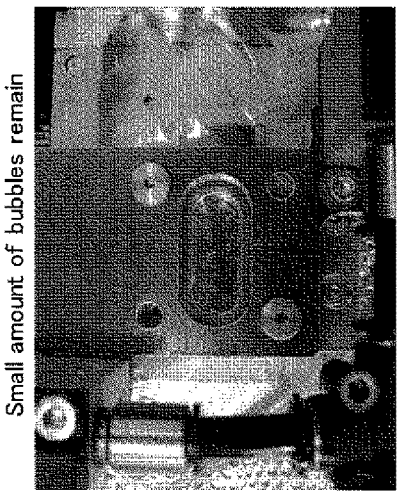
FIG. 11 (d) First (down, up, down) Small amount of bubbles remain
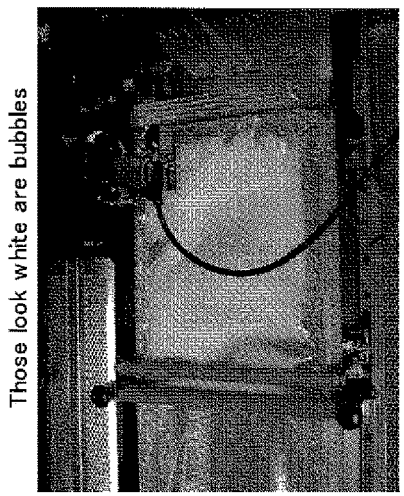
FIG. 11 (a) Those look white are bubbles
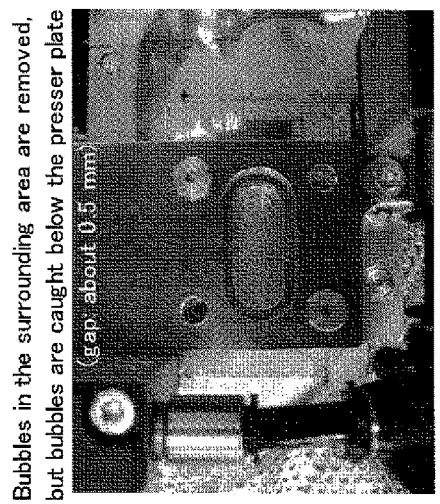
FIG. 11 (c) 0 (down) Bubbles in the surrounding area are removed, but bubbles are caught below the presser plate (gap: about 0.5 mm)

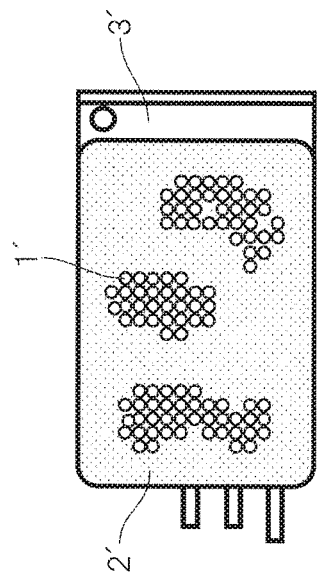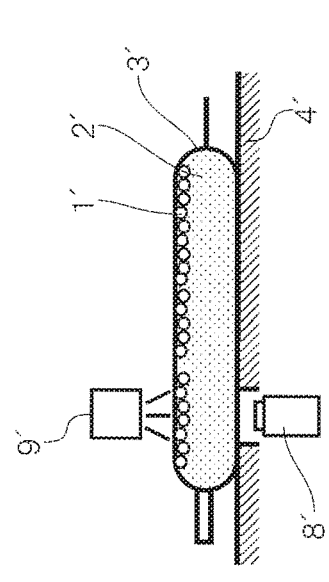
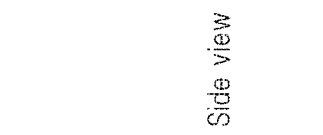
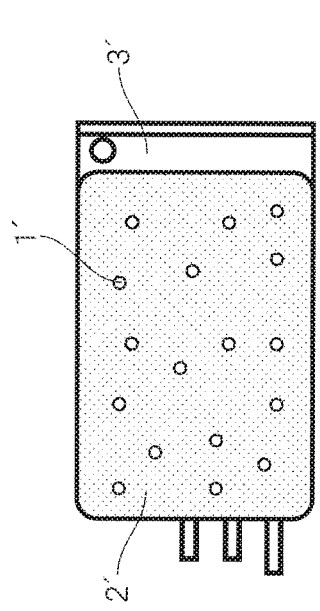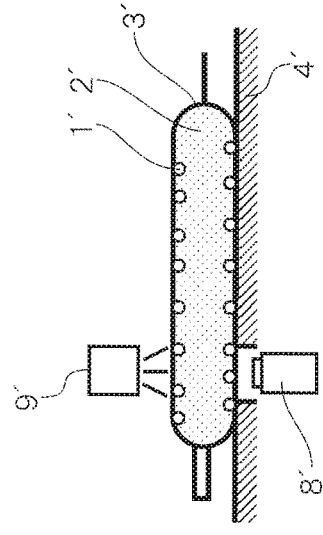
FIG. 13 (a) (Prior Art)    FIG. 13 (b) (Prior Art)

BUBBLE REMOVAL METHOD AND BUBBLE REMOVAL DEVICE

TECHNICAL FIELD

The present invention relates to a method for removing bubbles in a liquid. In particular, the present invention relates to a method for removing bubbles from a partial area of space in a container made of a soft package material in which a bubble-containing liquid is enclosed, as well as to an apparatus for removing bubbles.

BACKGROUND ART

In recent years, in the fields of production of medicines, gene therapy, regenerative medicine, immunotherapy or the like, it is required to culture efficiently a large amount of cells, tissues, microorganisms or the like in an artificial environment.

Under such circumstances, a large amount of cells is cultured automatically in a closed system by using a gas-permeable culture bag.

When cells are cultured for a long period of time, it is required to take photographs of cells in a culture bag at prescribed time intervals, thereby to observe periodically the number or the state of the cells. At this time, it is of crucial importance to obtain stable photographed images without fail.

However, since some culture liquids in a culture bag foam like soapy water, bubbles are also photographed when cells are photographed, and as a result, adequate counting or observation becomes impossible.

There are two main reasons that bubbles are generated in a culture bag. One reason is that a culture liquid in which oxygen and carbon dioxide have been dissolved in advance is enclosed in a culture bag. Therefore, when a culture liquid that has been stored in a refrigerator before use is warmed for use, these gases that have been dissolved may be generated in the form of bubbles. Another reason is that a film that forms a culture bag can pass oxygen and carbon dioxide therethrough. Accordingly, when a culture liquid in a culture bag is stirred by shaking a culture bag or by other methods in order to homogenize the culture liquid or for other purposes, the culture liquid foams by gases that have entered from outside through the film, and then bubbles are generated.

Therefore, as long as the thus generated bubbles are removed from an observation range, the bubbles are photographed when the inside of the container is photographed. As a result, a stable image cannot be obtained, leading to erroneous observation.

The constitution of a conventional culture bag observation apparatus and the manner of cell observation using such a conventional culture bag are shown in FIG. 12 and FIG. 13.

As shown in FIG. 12, in a conventional culture bag observation apparatus, a culture container 3' in which a culture liquid 2' containing bubbles 1' is enclosed is mounted on a mounting table 4'. The observation area of the culture container 3' is irradiated with light emitted from a lighting 9', and a photograph of cells in the container is taken by a photographing means 8'.

As mentioned above, since oxygen or carbon dioxide is dissolved in a culture liquid in advance, as shown in FIG. 13(a), these gases may be generated as bubbles. Such bubbles may often be relatively small. However, when an enlarged photograph of cells is taken by means of the photographing means 8' that is provided with a microscope and a camera, even small bubbles are photographed as big bubbles, and as a result, it greatly affects the observation. Therefore, even if small bubbles are generated, observation of cells could not be conducted adequately.

In the cell culture, a culture liquid in the culture bag is stirred. If such stirring is conducted, as shown in FIG. 13(b), gases that have passed through the film forming the culture bag foam by stirring, and as a result, bubbles are generated in the container. Such bubbles are relatively large, and often they are agglomerated. If cells are automatically photographed by the photographing means 8', it was almost impossible to conduct observation of cells.

Here, as the method for removing bubbles from a liquid, as stated in Patent Document 1, for example, a method can be given in which a pressure difference is provided in the flow path of the liquid in the container, and move of the bubbles is controlled, thereby to remove the bubbles. Further, as stated in Patent Documents 2 and 3, a method can be given in which bubbles in the liquid is removed by imparting ultrasonic vibration. Further, Patent Document 4 discloses that, by controlling a flow-control actuator, an additional culture liquid is supplied to a cell culture chamber, whereby bubbles are removed.

Patent Document 1: WO2007/077607
Patent Document 2: JP-A-2004-198356
Patent Document 3: JP-A-2009-31173
Patent Document 4: JP-A-H11-507229

However, the method described in Patent Document 1 is a method in which bubbles are removed while flowing a liquid. Therefore, it is not suited to cell culture utilizing a culture bag. By this method, it is impossible to observe the cells inside the culture bag adequately. Further, when ultrasonic wave is used as in the method disclosed in Patent Documents 2 and 3, cells may be adversely affected. If bubbles are removed by using a culture liquid to be added as disclosed in Patent Document 4, cells are also removed from the observation area simultaneously. Therefore, this method cannot be applied for the observation of cells.

As the method for removing bubbles from a liquid, in addition to the methods mentioned above, a method is conceived in which the temperature is lowered, the pressure is increased or the humidity is increased, relative to the state where bubbles are generated. Further, use of an anti-foaming agent is also conceivable.

However, in the cell culture using a culture bag, decreasing the temperature when removing bubbles in the culture bag causes the cell proliferation efficiency to be lowered. The pressure can be increased when a relatively small culture bag is used when cell culture starts, etc. However, when a large culture bag is used, increasing the pressure leads to an increase in size of an apparatus. Further, in the case of increasing the humidity, small bubbles are not generated easily, and hence, the amount of gases transmitted from the outside of the culture bag can also be reduced. Accordingly, the amount of large bubbles generated by stirring a culture liquid can also be reduced. However, this method causes molds to be generated easily. An anti-foaming agent may adversely affect the survival or proliferation of cells, and hence is not suited to be added to a culture liquid.

SUMMARY OF THE INVENTION

The inventors of the present invention made intensive studies. The inventors successfully removed bubbles outside an observation area by pressing from above a part of the upper surface of a container by means of a pressing member and by moving the pressing member. The invention has been attained based on this finding. According to one or more embodiments of this method, it becomes possible to remove bubbles automatically from an observation area without adversely affecting cells, and as a result, when cells in a culture bag are automatically photographed, an image in which no bubbles are photographed can be stably obtained. Further, such a method can be widely applied not only to cell culture but also to a case when bubbles are removed from a partial area of space in a container made of a soft package material in which a liquid is enclosed.

That is, one or more embodiments of the present invention is aimed at providing a method for removing bubbles in which bubbles are removed from an observation range when observing the inside of a container made of a soft package material enclosing a liquid that contains bubbles, as well as an apparatus for removing bubbles.

The method for removing bubbles in accordance with one or more embodiments of the present invention is a method for removing bubbles, in which, when observing the inside of a container that is made of a soft package material and encloses a liquid that contains bubbles, a part of space in the container is set to be an observation area to be observed and the bubbles are removed from the observation area, wherein the bubbles are pushed outside the observation area by pressing from above a part of the upper surface of the container that is positioned above the observation area by means of a pressing member and by moving the pressing member.

The apparatus for removing bubbles in accordance with one or more embodiments of the present invention is an apparatus for removing bubbles, wherein, when observing the inside of a container that is made of a soft package material and encloses a liquid that contains bubbles, the bubbles are removed from an observation area that is a part of space in the container, the apparatus comprises:

a mounting table provided with an observation range formed of a transparent member or a hole and specifies a part of space in the container positioned above the observation range as an observation area when the container is put on the mounting table;

a pressing member that presses from above the part of the upper surface of the container positioned above the observation area; and a driving unit that moves the pressing member; wherein the driving unit moves the pressing member to push the bubbles outside the observation area.

According to one or more embodiments of the invention, it becomes possible to remove bubbles from the observation area when observing the inside of a container made of a soft package material in which a liquid that contains bubbles is enclosed.

If cell culture is conducted by using a culture bag, it becomes possible to remove bubbles automatically from the observation area without adversely affecting cells. As a result, it becomes possible to photograph cells in a culture bag, thereby to obtain an image stably in which no bubbles are photographed.

BRIEF DESCRIPTION OF THE DRAWINGS

FIG. 1 is a view showing the outline of the method for removing bubbles in accordance with one or more embodiments of the present invention;

FIGS. 2(a) and (b) are views showing a first embodiment of the apparatus for removing bubbles according to the present invention;

FIGS. 3(a)-(c) are views showing steps of method 1 in the method for removing bubbles according to one or more embodiments of the present invention;

FIGS. 5(a)-(c) are views showing steps of method 2 in the method for removing bubbles according to one or more embodiments of the present invention;

FIGS. 6(a)-(c) are views showing steps of method 2' in the method for removing bubbles according to one or more embodiments of the present invention;

FIG. 8 is a view showing steps of method 3 in the method for removing bubbles according to one or more embodiments of the present invention;

FIGS. 9(a) and (b) are views showing a fifth embodiment of the apparatus for removing bubbles according to one or more embodiments of the present invention;

FIGS. 11(a)-(e) are photographs showing the results of the Examples of the present invention;

FIGS. 13(a) and (b) are views showing the state in which cells are observed by means of a conventional culture bag observation apparatus.

DETAILED DESCRIPTION OF EMBODIMENTS

Figure 4A:
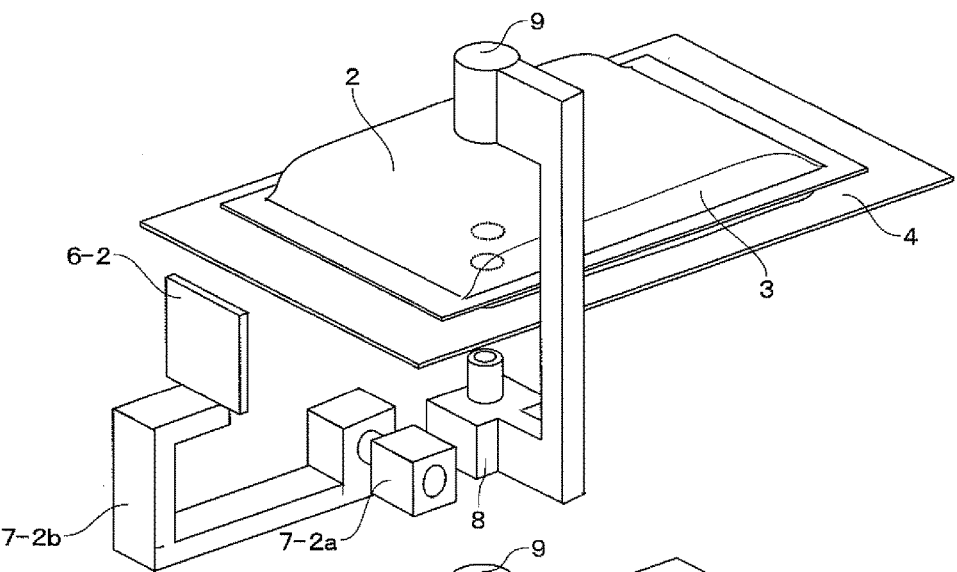
FIGS. 4(a) and (b) are views showing a second embodiment of the apparatus for removing bubbles according to the present invention.

Hereinbelow, an explanation will be made embodiments of the present invention.

First, the outline of the method for removing bubbles in accordance with one or more embodiments of of the present invention will be explained with reference to FIG. 1.

The method for removing bubbles in accordance with one or more embodiments of the present invention is a method in which, when observing the inside of a container that is made of a soft package material and encloses a liquid that contains bubbles, a part of space in the container is set to be an observation area, and the bubbles are removed outside from the observation area, wherein the bubbles are pushed outside the observation area by pressing from above a part of the upper surface of the container that is positioned above the observation area by means of a pressing member and by moving the pressing member.

Specifically, the following three methods can be given, which may be combined.

(Method 1: Horizontal Pressing Method)

The method 1 is a method in which a rod-like pressing member 6-1 is allowed to be horizontal and pressed against the upper surface of the container. Then, the rod-like pressing member 6-1 is moved in the horizontal direction to pass over an observation hole 5, i.e. over a part of the upper surface of a container 3 that is located above the observation area in the container 3, whereby bubbles are pushed outside the observation area.

(Method 2: Oblique Pressing Method)

The method 2 is a method in which, by using a plate-like pressing member 6-2 is used and pressed at an angle against a part of the upper surface of the container 3 that is above the observation hole 5. By moving rotationally the plate-like pressing member 6-2 until it becomes horizontal relative to the upper surface of the container, bubbles are pushed outside the observation area.

(Method 2': Oblique Pressing and Swinging method)

The method 2' is a method in which, the plate-like pressing member 6-2 is used and pressed at an angle against a part of the upper surface of the container 3 that is positioned above the observation hole 5. By swinging the plate-like pressing member 6-2 between a position where the pressing member is held at the angle and a position where the pressing member becomes horizontal with respect to the upper surface of the container, bubbles are pushed outside the observation area.

(Method 3: Repeated Up-Down Movement Method)

The method 3 is a method in which a plate-like pressing member 6-3 is used horizontally, and a part of the upper surface of the container 3 positioned above the observation area, that is above the observation hole 5, is pressed by means of the pressing member 6-3, whereby bubbles are pushed outside the observation area.

As mentioned above, when gases that have been dissolved in the culture liquid are generated as bubbles, small bubbles are mainly generated. Further, when gases that enter the culture bag by passing through the film from the outside foam to cause bubbles to be generated when stirring the culture liquid, relatively large bubbles may tend to be generated. In the specification of this application, small bubbles mean bubbles having a diameter of about 0.1 mm or less, and large bubbles mean bubbles having a diameter of larger than about 0.1 mm.

Large bubbles can be efficiently removed by any of methods 1, 2, 2' and 3.

Small bubbles, in particular, those having a diameter of about several tens μm may be stuck to the inner surface of a culture bag, and is hardly moved. Normally, observation of cells is conducted by taking a microphotograph. As mentioned above, even in the case of small bubbles, it exerts a significant effect when they are enlarged since they have a larger size as compared with that of cells. When removal of bubbles is conducted by method 1 or method 2, small bubbles that have not been adhered to the inner surface of a culture bag can be removed. However, small bubbles adhering to the inner surface of a culture bag are difficult to be removed. On the other hand, in the case of removal by method 2' or method 3, it is possible to remove small bubbles efficiently. Further, by using them in combination, it becomes possible to remove bubbles more efficiently from the observation area.

[First Embodiment]

Next, the method for removing bubbles and the constitution of the apparatus for removing bubbles according to the first embodiment of the present invention will be explained with reference to FIG. 2 and FIG. 3. The apparatus for removing bubbles of this embodiment can be used when the method for removing bubbles of the above-mentioned method 1 is conducted.

That is, the apparatus for removing bubbles according to this embodiment comprises, as shown in these figures, a container 3 in which a liquid 2 that contains bubbles 1 is enclosed, a mounting table 4 on which this container 3 is mounted, a rod-like pressing member 6-1 that presses the upper surface of the container 3, and a driving unit 7-1 that allows this rod-like pressing member 6-1 to move horizontally.

No specific restrictions are imposed on the container 3 as long as it is a bag-like container made of a soft package material and is capable of enclosing a liquid. Since the container serves to remove bubbles from the observation range by moving the bubbles in the liquid, the container can be formed of a transparent material. Further, by using a soft package material as the material of the container 3, flexibility and softness can be imparted to the container 3. Therefore, by pressing the container 3 by means of the pressing member, it is possible to move bubbles in the container 3.

When the container 3 is used as a container for cell culture, it may have gas permeability that is necessary for cell culture. Further, in order to be able to confirm the contents, part or all of the container may have transparency. As the material that satisfies such requirements, for example, polyolefin, an ethylene-vinyl acetate copolymer, a styrene-based elastomer, a polyester-based thermoplastic elastomer, a silicone-based thermoplastic elastomer, silicone rubber or the like can be mentioned.

The liquid 2 to be enclosed in the container 3 is not particularly restricted. Any liquid is possible as long as it generates bubbles. When the method for removing bubbles of this embodiment is used in cell culture, as the liquid 2, a culture liquid of cells is used. However, in the cell culture liquid, bubbles tend to be generated easily. That is, since oxygen and carbon dioxide are dissolved in a culture liquid, they tend to be generated as bubbles easily. Further, one having gas permeability is used as the material of the container 3, bubbles tend to be generated easily by gases transmitted to the container 3 from outside.

The mounting table 4 is a flat table that carries the container 3 on the upper surface thereof. The mounting table 4 has the observation hole 5 as an observation range, and a part of space in the container 3 positioned above the observation range is specified as an observation area. The observation hole 5 allows an observation of the inside of the container 3 therethrough by means of an observation unit 8 or the like. The observation range of the mounting table 4 may be formed of a transparent material instead of the observation hole 5. Various configurations for fixing the container 3 to the mounting table 4, such as a fixture for fixing the container 3 to the mounting table 4, may be provided in the mounting table 4.

A rod-like pressing member 6-1 is a pressing member that moves on the container 3 in the horizontal direction while pressing a part of the upper surface of the container 3 from above in a configuration in which the longitudinal direction thereof becomes horizontal. No specific restrictions are imposed on the rod-like pressing member 6-1 as long as bubbles are pushed outside the observation area by such an operation. For example, as shown in FIGS. 2 and 3, a roller may be used.

That is, in these figures, the rod-like pressing member 6-1 is formed in the shape of a cylindrical form, and is arranged on the upper surface of the container 3 such that the axial direction thereof becomes in parallel with the width direction of the container 3. Due to such a configuration, the rod-like pressing member 6-1 can be moved by rotation horizontally along the longitudinal direction of the container 3. The rod-like pressing member 6-1 is configured such that the length in the axial direction thereof is longer than the width of the container 3.

The rod-like pressing member 6-1 passes a region above the observation hole 5, i.e. a region of the container 3 above the observation area, while pressing the upper surface of the container 3. As a result, by the movement of the rod-like pressing member 6-1, bubbles can be moved within the container 3, and removed outside the observation area.

The driving unit 7-1 is a rod-like horizontal moving means that is connected to the rod-like pressing member 6-1 and allows it to move in the horizontal direction. The driving unit 7-1 is not particularly restricted as long as it can move the rod-like pressing member 6-1 in the horizontal direction while pressing from above the container 3. For example, as shown in FIG. 2, it can be configured such that it is provided with an electrically-operated driving part 7-1a and a supporting part 7-1b that is connected to the rod-like pressing member 6-1 and is moved by the driving part 7-1a.

In the figure, the supporting part 7-1b is arranged upwardly on one side of the mounting table 4, and is connected to the edge part of the rod-like pressing member 6-1 to support the rod-like pressing member 6-1. A configuration may be possible in which this supporting part 7-1b is provided on the both sides of the mounting table 4. Further, the supporting part 7-1b is connected to the driving part 7-1a. By moving this supporting part 7-1b in the horizontal direction by means of the driving part 7-1a, it is possible to allow the rod-like pressing member 6-1 connected to the supporting part 7-1b to move horizontally at the horizontal position at which the container 3 is pressed from above, whereby bubbles within the container 3 can be moved. A driving part that moves the supporting part 7-1b in the up-and-down direction may be further provided in the driving apparatus 7-1, thereby to allow the horizontal position at which the container 3 is pressed to be changed easily.

As such driving part, an electrically-operated cylinder (an actuator for horizontal movement or an actuator for vertical movement) can be used. Instead of the electrically-operated actuator, it is possible to use an actuator utilizing pneumatic pressure, hydraulic pressure or electromagnetic force. A configuration in which a motor or a cam is used is possible.

In the above-mentioned example, the pressing member is moved on the container 3. However, it is possible to configure such that the container 3 is moved with the pressing member being fixed. The same can be applied to the following embodiments.

When the apparatus for removing bubbles of this embodiment is used for cell culture, the apparatus may be provided with an observation unit 8 for photographing cells in the container 3 through the observation range (an observation hole 5 or a transparent member) provided in the mounting table 4 and a lightening 9 that illuminates the observation area in the container 3.

The observation unit 8 is a microscope provided with a camera function, and cells in the container 3 are automatically photographed through the observation range in a fixed time period. Further, also not shown in the figure, data of images obtained by photographing are inputted into an information processing apparatus, and the number of cells in the image is counted. As for the observation unit 8, the automatic photographing method, and the method for counting cells, those commonly used at present can be used. The camera function may be provided separately from the microscope main body.

The lighting 9 is provided on the side opposite to the observation unit 8 relative to the mounting table 4. The observation area in the container 3 that is positioned above the observation range of the mounting table 4 is irradiated with light, whereby light in an amount necessary for photographing by means of the observation unit 8 is supplied.

As shown in FIG. 3, the method for removing bubbles of this embodiment, is a method in which bubbles in the container 3 are removed by using such apparatus for removing bubbles. That is, while pressing the upper surface of the container 3 by the rod-like pressing member 6-1, the rod-like pressing member 6-1 is allowed to move horizontally, whereby it is allowed to pass above the observation hole 5 of the mounting table 4. As a result, bubbles in the container 3 can be removed from the observation area that is positioned above the observation hole 5 of the mounting table 4, whereby the inside of the container 3 can be stably photographed by the observation unit 8.

As mentioned above, according to the method for removing bubbles and the apparatus for removing bubbles of this embodiment, it is possible to move bubbles in the container 3 and remove them from the observation area. As a result, in particular when bubbles are relatively large, it becomes possible to remove bubbles efficiently from the observation area.

[Second Embodiment]

Figure 4B:
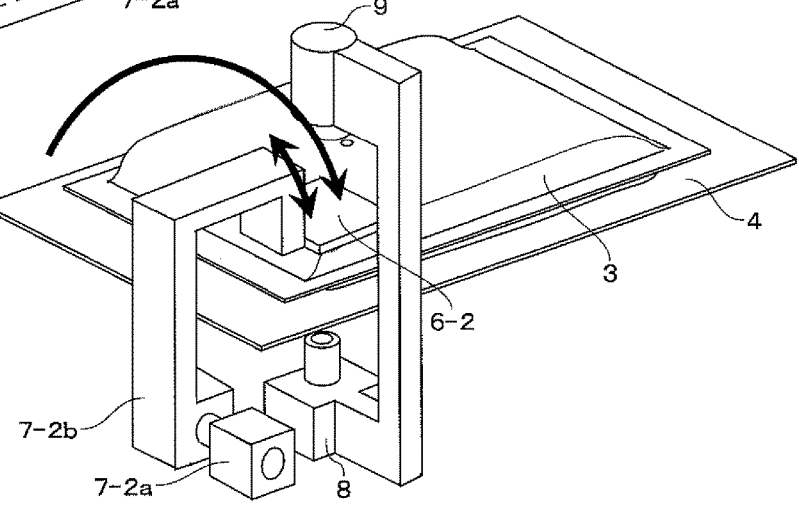

Next, an explanation will be made on the method for removing bubbles and the apparatus for removing bubbles of the second embodiment of the invention with reference to FIGS. 4 and 5. The apparatus for removing bubbles of this embodiment can be used when the method for removing bubbles according to the method 2 is conducted.

That is, as shown in these figures, the apparatus for removing bubbles of this embodiment is provided with the container 3 in which the liquid 2 that contains the bubbles 1 is enclosed, the mounting table 4 on which this container 3 is mounted, a plate-like pressing member 6-2 that presses the upper surface of the container 3 and a driving unit 7-2 that rotationally moves this plate-like pressing member 6-2.

As for the container 3 and the mounting table 4, the same container and mounting table as those in the first embodiment can be used. The same can be applied to the following embodiments.

The plate-like pressing member 6-2 is an inclined pressing member that moves rotationally until it becomes horizontal relative to the horizontal surface while pressing the upper surface of the container 3 at an angle relative to the horizontal surface. No particular restrictions are imposed on the plate-like pressing member 6-2, as long as it can remove bubbles outside the observation area. For example, in addition to a member having a rectangular horizontal surface as shown in FIGS. 4 and 5, members having various shapes can be used. FIG. 4 shows a relatively small plate-like pressing member 6-2, and FIG. 5 shows a transparent plate-like pressing member 6-2 of which the long side is longer than the width of the container 3.

The plate-like pressing member 6-2 is pressed at an angle to a region of the upper surface of the container 3 right above the observation area on such that it covers the region in the state in which it becomes horizontal.

As shown in these figures, in the state where the plate-like pressing member 6-2 is inclined relative to the horizontal surface of the container 3, by allowing the plate-like pressing member 6-2 to move by rotation until it becomes horizontal while pressing the upper surface of the container 3 by means of the plate-like pressing member 6-2, bubbles are moved upwardly in the container 3 along the plate-like pressing member 6-2. As a result, bubbles can be moved outside the observation area The driving unit 7-2 is a plate-like member rotation movement means that is connected with the plate-like pressing member 6-2 and allows it to move by rotation. No specific restrictions are imposed on the driving unit 7-2 as long as it can press the upper surface of the container 3 obliquely by the rotational move of the plate-like pressing member 6-2. For example, as shown in FIG. 4, it can be a pressing member that is provided with an electrically-operated driving part 7-2a and a supporting part 7-2b that is connected to the plate-like pressing member 6-2 and is moved by means of the driving part 7-2a.

In this figure, the supporting part 7-2b is connected to the plate-like pressing member 6-2 at one end, and is connected to the driving part 7-2a at the other end through a rotating shaft. By allowing the driving part 7-2a to rotate the supporting part 7-2b, while pressing the upper surface of the container 3 obliquely from above, the plate-like pressing member 6-2 can be rotationally moved.

As the driving part 7-2a, an electrically-operated actuator for rotational driving can be used. Instead of an electrically-operated actuator, pneumatic pressure, hydraulic pressure, electromagnetic force or the like can be used.

When the apparatus for removing bubbles of this embodiment is used for cell culture, the apparatus may be provided with the same observation unit 8 and the lightening 9 as those of the first embodiment. The same can be applied to the following embodiments.

As shown in FIG. 5, the method for removing bubbles of this embodiment is a method in which bubbles in the container 3 are removed from the observation area by using such an apparatus for removing bubbles, or the like. That is, the plate-like pressing member 6-2 is pressed at an angle against a region of the upper surface of the container 3 right above the observation area, the plate-like pressing member 6-2 is allowed to move rotationally until it becomes horizontal relative to the upper surface of the container 3. As a result, it is possible to remove bubbles in the container from the observation area in the observation hole 5 in the mounting table 4, whereby photographing of the inside of the container 3 by the observation unit 8 can be conducted stably.

According to the method for removing bubbles and the apparatus for removing bubbles of this embodiment, in particular when bubbles are relatively large, bubbles can be efficiently removed from the observation area.

[Third Embodiment]

The method for removing bubbles and the configuration of the apparatus for removing bubbles of the third embodiment of the invention will be explained with reference to FIG. 6. The method for removing bubbles of this embodiment is the method 2' mentioned above. As the apparatus for removing bubbles, the same apparatus as that in the second embodiment can be used.

As shown in FIG. 6, in the method for removing bubbles of this embodiment, the plate-like pressing member 6-2 is pressed at an angle against a region of the upper surface of the container 3 right above the observation area. Between a position at which the plate-like pressing member 6-2 is held at the angle and a position at which the pressing member 6-2 becomes horizontal relative to the upper surface of the container 3 as a result of rotational movement, the plate-like pressing member is subjected to a swinging movement. At this time, the swinging is conducted such that the pressing member taps the container 3 with a fine and quick operation.

The speed for subjecting the plate-like pressing member 6-2 to a swing movement may be about 50 mm/sec to 500 mm/sec. If the speed is slower than 50 mm/sec, bubbles are not moved sufficiently. On the other hand, if the speed is faster than 500 mm/sec, the inside of the container 3 is vigorously stirred, and as a result, there is a concern that cells will be damaged, and a heavy load will be applied to the apparatus.

The frequency of allowing the plate-like pressing member 6-2 to swing is not particularly restricted, and can be appropriately set in accordance with the amount of bubbles generated in the container 3. Further, it is possible to allow it to standstill for a prescribed time period every single reciprocal movement.

As mentioned above, according to the method for removing bubbles and the apparatus for removing bubbles of this embodiment, by swinging the plate-like pressing member 6-2, it is possible to move bubbles below the plate-like pressing member 6-2 to the surrounding area. Therefore, according to this embodiment, even if bubbles are small, it is possible to remove them efficiently from the observation area.

[Fourth Embodiment]

Figure 7:
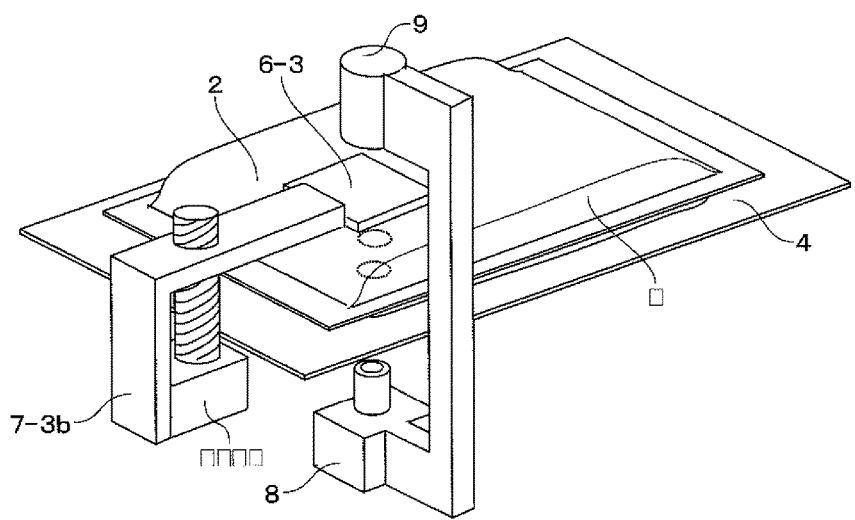
FIGS. 7(a) and (b) are views showing a fourth embodiment of the apparatus for removing bubbles according to one or more embodiments of the present invention.
Figure 7:
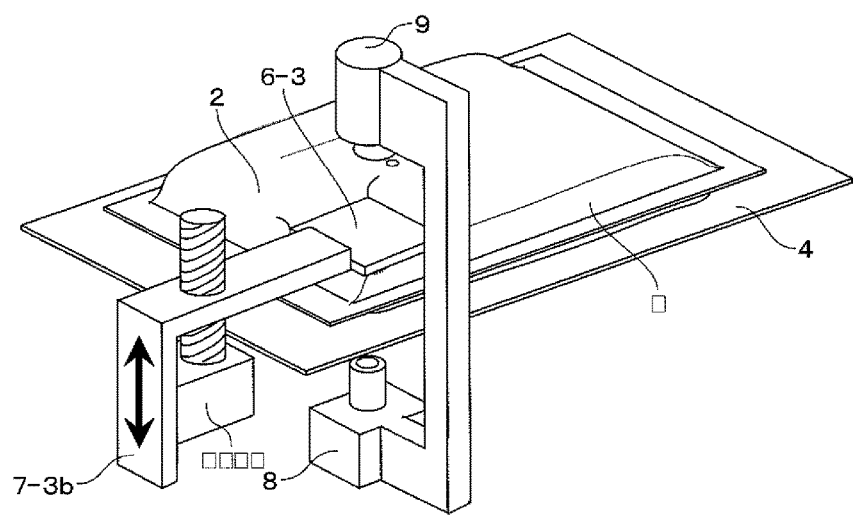

Next, an explanation will be made on the method for removing bubbles and the configuration of the apparatus for removing bubbles of the fourth embodiment with reference to FIGS. 7 and 8. The apparatus for removing bubbles of this embodiment can be used when the method for removing bubbles of the above-mentioned method 3 is implemented.

That is, as shown in these figures, the apparatus for removing bubbles of this embodiment is provided with the container 3 in which the liquid 2 containing the bubbles 1 is enclosed, the mounting table 4 on which this container 3 is mounted, the plate-like pressing member 6-3 that is pressed against the upper surface of the container 3, and a driving unit 7-3 that moves this plate-like pressing member 6-3.

The plate-like pressing member 6-3 is a tapping member that is pressed against a part of the upper surface of the container 3 horizontally, and presses the upper surface of the container 3 by repeatable up-and-down movement. No specific restrictions are imposed on the plate-like pressing member 6-3 as long as it can push bubbles outside the observation area by this movement. In addition to one having a rectangular horizontal surface as shown in FIG. 7, those having various shapes can be used.

The plate-like pressing member 6-3 is arranged above the observation hole 5 of the mounting table 4, i.e. above the observation area in the container 3, and presses a region including a region right above the observation area on the upper surface of the container 3.

The driving unit 7-3 is connected to the plate-like pressing member 6-3, and serves to allow this plate-like pressing member 6-3 to move reciprocally in the vertical direction, and is a plate-like up-and-down movement means. No particular restrictions are imposed on the driving unit 7-3 as long as it can stir the inside of the container 3 by allowing the plate-like pressing member 6-3 to move reciprocally in the up-and-down direction. However, as shown in FIG. 6, for example, it is possible to use one that drives a supporting part 7-3b connected to the plate-like pressing member 6-3 by means of an electrically-operated cylinder (an actuator for the movement in the vertical direction). Further, instead of the electrically-operated actuator, it is possible to use an actuator utilizing pneumatic pressure, hydraulic pressure or electromagnetic force. A configuration in which a motor or a cam is used is also possible.

In the method for removing bubbles of this embodiment, by using such an apparatus for removing bubbles or the like, bubbles can be removed from the observation area by the steps shown in FIG. 8.

That is, at first, the plate-like pressing member 6-3 is moved downwardly from a position above the container 3, whereby the upper surface of the container 3 above the observation hole 5 of the mounting table 4 is pressed. Subsequently, a reciprocal movement in which the plate-like pressing member 6-3 is moved upward, and then, the plate-like pressing member 6-3 is moved downward, is repeated at least one or more times. The reciprocal movement is stopped at a position where the plate-like pressing member 6-3 is moved downward.

If the plate-like pressing member 6-3 is moved downward in the state where it presses the upper surface of the container 3, the bubbles 1 are flown from a region below the plate-like pressing member 6-3 to the surrounding area together with the liquid 2 in the container 3. As a result, the bubbles 1 are removed from the observation area. Further, if the plate-like pressing member 6-3 is moved upward in the state where it presses the upper surface of the container 3, the liquid 2 in the surrounding area is drawn into the observation area, whereby the bubbles 1 adhering to the inner surface of the container 3 can be peeled off.

As mentioned above, according to the method for removing bubbles of this embodiment, it is possible to form a flow of a liquid through which bubbles are moved in the container 3, and as a result, it is possible to efficiently remove small bubbles adhering to the inner surface of the container 3.

The distance between the plate-like pressing member 6-3 and the bottom surface of the container 3 when the plate-like pressing member 6-3 is moved downward from a position above the container 3, or the width of the up-and-down movement of the plate-like pressing member 6-3 can be appropriately determined in accordance with the amount of the liquid 2 enclosed in the container 3 or the thickness of the container 3.

For example, when a 230 mm×300 mm cell culture container is filled with 250 ml of a culture liquid, the thickness of the liquid will be about 5 mm. By allowing the distance between the plate-like pressing member 6-3 and the bottom surface of the container 3 to be 1 mm or less and the width of the up-and-down movement of the plate-like pressing member 6-3 to be 5 mm or more, bubbles can be removed.

The speed at which the plate-like pressing member 6-3 is moved reciprocally is about 50 mm/sec to 500 mm/sec. If the speed is slower than 50 mm/sec, bubbles cannot be moved sufficiently. On the other hand, if the speed is faster than 500 mm/sec, the inside of the container 3 is vigorously stirred, and as a result, there is a concern that cells will be damaged, and a heavy load will be applied to the apparatus.

Further, the number of reciprocal movement of the plate-like pressing member 6-3 is not particularly restricted, and can be appropriately set according to the amount of bubbles generated in the container 3. In addition, it can be brought into a standstill for a predetermined period of time at every reciprocation.

As mentioned above, according to the method for removing bubbles and the apparatus for removing bubbles of this embodiment, by allowing the plate-like pressing member 6-3 to move up and down repeatedly, it is possible to move bubbles below the plate-like pressing member 6-3 to the surrounding area. As a result, according to this embodiment, even if bubbles are small, it becomes possible to remove efficiently from the observation area.

[Fifth Embodiment]

Next, an explanation will be made on the method for removing bubbles and the configuration of the apparatus for removing bubbles of the fifth embodiment with reference to FIG. 9. The apparatus for removing bubbles of this embodiment has a configuration that is a combination of the first embodiment and the second embodiment. It can be used when bubbles are removed by implementing both the method 1 and the method 2 mentioned above.

The apparatus for removing bubbles of this embodiment is provided with the container 3 in which the liquid 2 that contains the bubbles 1 is enclosed, the mounting table 4 on which this container 3 is mounted, the rod-like pressing member 6-1 that presses the upper surface of the container 3, the driving unit 7-1 that moves this rod-like pressing member 6-1, the plate-like pressing member 6-2 that presses the upper surface of the container 3 and the driving unit 7-2 that allows the plate-like pressing member 6-2 to move. As for the configuration of each of these, the same as those in the first embodiment and the second embodiment can be used.

The method for removing bubbles of this embodiment is not particularly restricted as long as it can implement both of the method 1 and the method 2. For example, the method can be one that comprises the following steps and uses the apparatus for removing bubbles of this embodiment.

First, the driving unit 7-1 is driven, and the rod-like pressing member 6-1 is moved in the horizontal direction, and is allowed to pass a region of the upper surface of the container 3 right above the observation area while pressing this region. In FIG. 9, the horizontal position of the rod-like pressing member 6-1 is adjusted in advance to a position where the container 3 on the mounting table 4 is adequately pressed. By moving the rod-like pressing member 6-1 in the horizontal direction, it is possible to allow it to move while pressing the container 3 from above. As a result, bubbles can be removed outside the observation area in the container 3.

Next, the driving unit 7-2 is driven, and in the state where the plate-like pressing member 6-2 is held at an angle relative to the horizontal direction, a region including a region of the upper surface of the container 3 right above the observation area is pressed from above, and the plate-like pressing member 6-2 is allowed to move rotationally until it becomes horizontal. As a result, it is possible to allow bubbles to move upward in the container 3 along the bottom surface of the plate-like pressing member 6-2, whereby bubbles can be expelled from the region below the plate-like pressing member 6-2, and can be removed from the observation area in the container 3.

As mentioned above, according to the method for removing bubbles and the apparatus for removing bubbles of this embodiment, after bubbles are removed from the observation area by moving the rod-like pressing member 6-1 in the horizontal direction while pressing the container 3 by the rod-like pressing member 6-1, in the state being held at an angle with respect to the horizontal direction, the plate-like pressing member 6-2 is allowed to move rotationally while pressing the container 3 from above until it becomes horizontal. As a result, even if bubbles remain in the observation area after the removal of bubbles by the rod-like pressing member 6-1, removal of remaining bubbles can be conducted by the plate-like pressing member 6-2.

Therefore, according to this embodiment, as compared with a case where each of the first embodiment and the second embodiment is conducted individually, removal of bubbles can be performed with a high degree of accuracy.

Further, bubbles may be removed from the observation area in the container 3 by implementing both the method 1 and the method 2' mentioned above by using the apparatus for removing bubbles of this embodiment. According to this method, as compared with a case where both the method 1 and the method 2 are implemented, small bubbles can be removed more efficiently, whereby removal of bubbles can be conducted with a higher degree of accuracy.

[Sixth Embodiment]

Figure 10A:
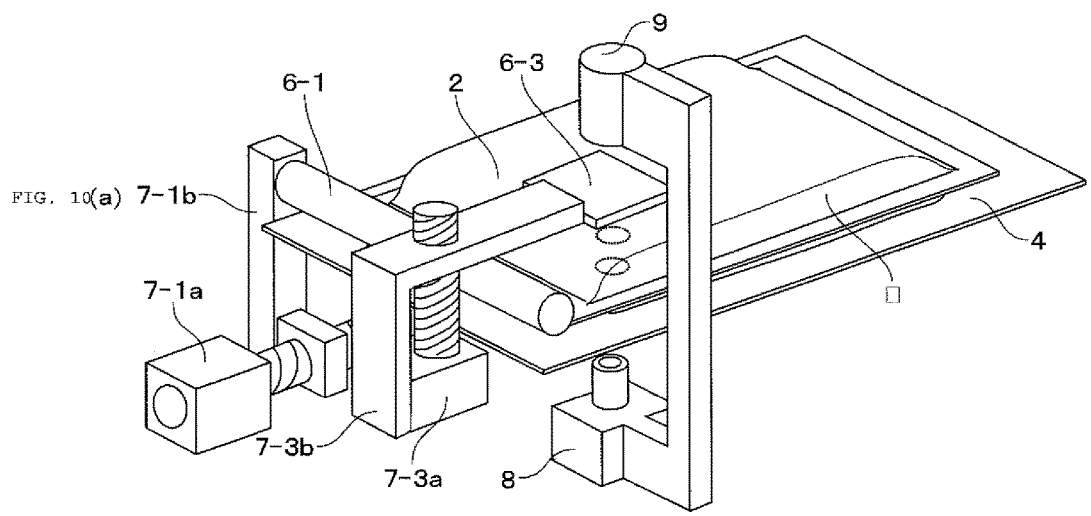
FIGS. 10(a) and (b) are views showing a sixth embodiment of the apparatus for removing bubbles according to one or more embodiments of the present invention.
Figure 10B:
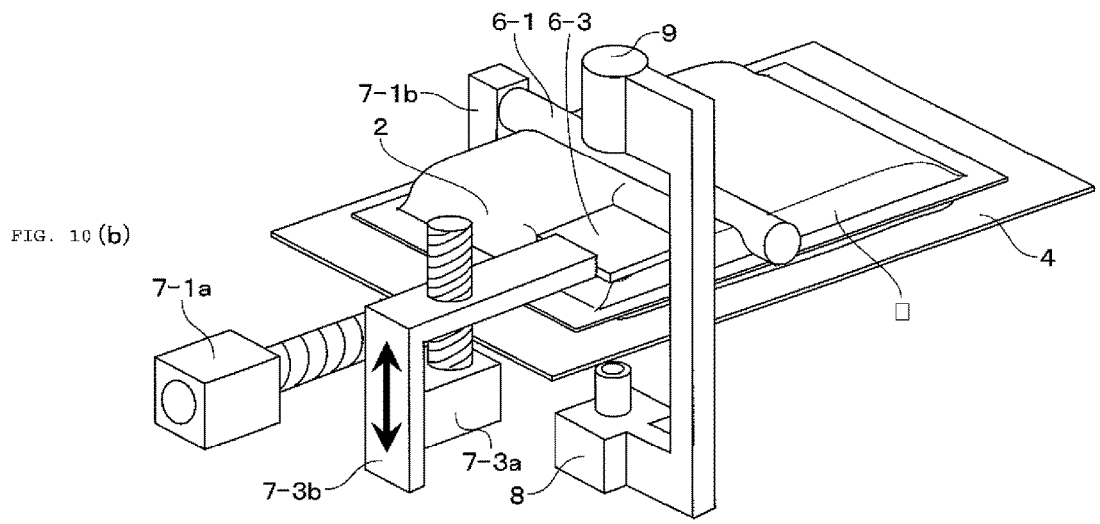
Figure 12:
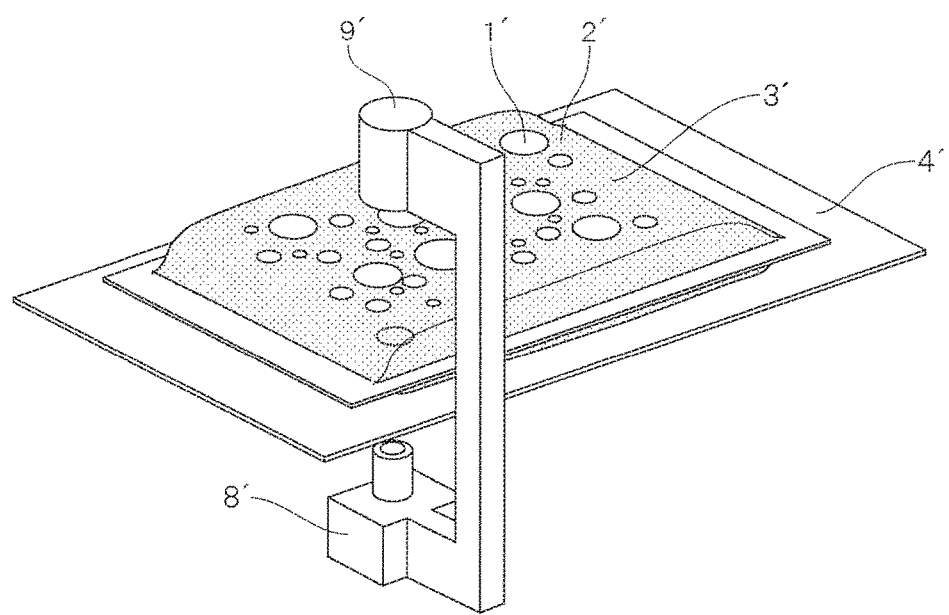
FIG. 12 is a photograph showing a conventional culture bag observation apparatus.

Next, an explanation will be made on the method for removing bubbles and the configuration of the apparatus for removing bubbles of the sixth embodiment with reference to FIG. 10. The apparatus for removing bubbles of this embodiment has a configuration that is a combination of the first embodiment and the fourth embodiment. It can be used when bubbles are removed by implementing both the method 1 and the method 3 mentioned above.

The apparatus for removing bubbles of this embodiment is provided with the container 3 in which the liquid 2 that contains the bubbles 1 is enclosed, the mounting table 4 on which this container 3 is mounted, the rod-like pressing member 6-1 that presses the upper surface of the container 3, the driving unit 7-1 that moves this rod-like pressing member 6-1, the plate-like pressing member 6-3 that presses the upper surface of the container 3 and the driving unit 7-3 that moves the plate-like pressing member 6-3. As for the configuration of each of these, the same as those in the first embodiment or the fourth embodiment can be used.

No specific restrictions are imposed on the method for removing bubbles of this embodiment as long as it can implement both the method 1 and the method 3. For example, the method can be one that comprises the following steps and uses the apparatus for removing bubbles of this embodiment.

First, as in the case of the fifth embodiment, the driving unit 7-1 is driven to allow the rod-like pressing member 6-1 to move in the horizontal direction, and is allowed to pass a region of the upper surface of the container 3 right above the observation area while pressing this region. As a result, when small bubbles and relatively large bubbles are generated in the container 3, small bubbles that are not adhering to the inner surface of the container 3 and relatively large bubbles can be moved and removed outside the observation area in the container 3.

Subsequently, the driving apparatus 7-3 is driven to allow the plate-like pressing member 6-3 to move in the up-and-down direction repeatedly. For example, the plate-like pressing member 6-3 is allowed to move downward to press the upper surface of the container 3. Subsequently, in the state where the upper surface of the container 3 is pressed, the plate-like pressing member 6-3 can be moved reciprocally in the up-and-down direction twice. Further, the number of reciprocal movement of the plate-like pressing member 6-3 is not particularly restricted, and can be appropriately set according to the amount of bubbles generated in the container 3. It may be once or three times or more. As a result, small bubbles adhering to the inner surface of the container 3 can be moved to the outside of a region below the plate-like pressing member 6-3, and can be removed outside the observation area in the container 3.

As mentioned above, according to the method for removing bubbles and the apparatus for removing bubbles of this embodiment, first, bubbles that can be moved relatively easily are moved in the horizontal direction while pressing the container 3 by means of the rod-like pressing member 6-1, thereby to remove them from the observation area. Subsequently, by allowing the plate-like pressing member 6-3 to move in the up-and-down direction while pressing the container 3 by the plate-like pressing member 6-3, small bubbles that adhere to the inner surface of the container 3 and cannot be moved easily can be removed from the observation area.

Accordingly, even if large bubbles and small bubbles are generated in the container 3, they can be removed efficiently.

EXAMPLES

Example 1

By using the method for removing bubbles and the apparatus for removing bubbles of the fourth embodiment, an experiment was conducted for removing bubbles from the container in which a liquid that contains bubbles is enclosed.

As the container, a bag made of LLDPE (linear low-density polyethylene) with a dimension of 230 mm×300 mm (film thickness: 0.1 mm) was used. As for the liquid, to 250 cc of water and 1 cc of a liquid detergent for washing dishes, 10 cc of air was mixed. The resultant was put and sealed in a container, and was allowed to foam until it looked white. The thickness of the bag after the liquid was sealed was about 5 mm.

As the plate-like pressing member, a stainless-made member having a dimension of 40 mm×40 mm and having a glass observation window was used. As the driving unit, an air cylinder (manufactured by Koganei Corporation) was used. Then, the plate-like pressing member was pressed until the distance between the bottom thereof and the bottom of the container became 1 mm, and moved twice in the up-and-down direction with a width of 5 mm. At this time, the speed of the up-and-down movement of the plate-like pressing member was about 100 mm/sec. The results are shown in FIG. 11. In this figure, the state of bubbles can be confirmed visually.

First, as shown in FIG. 11($a$), it can be confirmed that the soapy water in the container was foaming white, showing that bubbles are present throughout the container.

FIG. 11($b$) shows the state of the observation area in the container before pressing. It can be confirmed that it was white turbid, and contained a large amount of bubbles.

FIG. 11($c$) shows the state where the plate-like pressing member is moved downward and presses the container. It can be confirmed that a part of bubbles in the observation area is removed, but bubbles are still present below (about 0.5 mm space) the plate-like pressing member.

FIG. 11($d$) shows the state immediately after the single reciprocal up-and-down movement of the plate-like pressing member. It can be confirmed that a slight amount of bubbles remains.

FIG. 11($e$) shows the state immediately after the twice reciprocal up-and-down movements of the plate-like pressing member. It can be confirmed that bubbles are removed from the observation area.

From this example, it can be understood that, according to one or more embodiments of the method for removing bubbles and the apparatus for removing bubbles of the present invention, when observing the inside of a container made of a soft package material in which a liquid containing bubbles is enclosed, by allowing a pressing member to move while pressing a region of the upper surface of the container right above the observation area, it is possible to push bubbles efficiently outside the observation area.

The present invention is not limited to the above-mentioned embodiments and the example, and various modifications are possible within the scope of the present invention.

For example, as is apparent from the example, besides cell culture, one or more embodiments of the present invention can be widely used in the case where a liquid is enclosed in a container made of a soft package material and bubbles are required to be removed from a partial region of the container. Further, it is possible that, by combining the second embodiment and the fourth embodiment, a container is pressed from above by a plate-like pressing member that is held at an angle relative to the horizontal direction, and the pressing member is allowed to be horizontal by rotational movement, and then this plate-like pressing member is moved up and down. Further, it is also possible that, by combining the third embodiment and the fourth embodiment, a plate-like pressing member is subjected to a swing movement between a position at which the plate-like pressing member is held at an angle relative to the horizontal direction and a position at which the plate-like pressing member is moved by rotation until the pressing member becomes horizontal relative to the upper surface of the container, and then this plate-like pressing member is moved up and down.

INDUSTRIAL APPLICABILITY

One or more embodiments of the present invention can be used when an observation is conducted by automatically photographing cells when a large amount of cells is cultured by using a cell culture container. In addition, one or more embodiments can be used when a liquid is enclosed in a container made of a soft package material and bubbles are required to be removed from a partial region of the container.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENTIAL NUMERALS

1 Bubbles
2 Liquid
3 Container
4 Mounting table
5 Observation hole
6-1 Rod-like pressing member
6-2 Plate-like pressing member
6-3 Plate-like pressing member
7-1, 7-2 and 7-3 Driving unit
7-1a, 7-2a and 7-3a Driving part
7-1b, 7-2b and 7-3b Supporting part
8 Observation unit
9 Lightening

The invention claimed is:
1. A method for removing bubbles from an observation area that is a part of space in a container, the method comprising:
    pressing a pressing member horizontally placed on a part of an upper surface of the container that is positioned above the observation area,
        wherein the pressing member is a plate-like member, and
        wherein the container is made of a soft package material and encloses a liquid comprising the bubbles;
    providing a reciprocal movement of the pressing member one or more times so as to push the bubbles outside the observation area,
        wherein each reciprocal movement comprises moving the pressing member from an upper side of the container to a lower side of the container, moving the pressing member from the lower side to the upper side, and moving the pressing member from the upper side to the lower side; and
    stopping the pressing member at a position where the pressing member is moved at the lower side.
2. The method for removing bubbles according to claim 1, the method further comprising, prior to providing the reciprocal movement:
    pressing the pressing member at an angle against the part of the upper surface of the container that is positioned above the observation area; and
    moving the pressing member until the pressing member becomes horizontal relative to the upper surface of the container.
3. The method for removing bubbles according to claim 1, the method further comprising, prior to providing the reciprocal movement:
    pressing the pressing member at an angle against the part of the upper surface of the container that is positioned above the observation area; and
    swinging the pressing member between a position where the pressing member is held at the angle and a position where the pressing member is horizontal relative to the upper surface of the container.
4. The method for removing bubbles according to claim 1, the method further comprising:
    pressing a rod-like member horizontally against the upper surface of the container, and
    moving the rod-like member in the horizontal direction so as to pass the pressing members over the part of the upper surface of the container that is positioned above the observation area.
5. An apparatus for removing bubbles from an observation area that is a part of space in a container, the apparatus comprising:
    a mounting table comprising an observation range formed of a transparent member or a hole for observing a part of space in the container that is positioned above the observation range as an observation area when the container is put on the mounting table;
    a pressing member that presses a part of an upper surface of the container that is positioned above the observation area, wherein the pressing member is a plate-like member;
    and a driving unit that moves the pressing member so as to push the bubbles outside the observation area, wherein the driving unit is configured to perform:
    pressing the pressing member horizontally placed on the part of the upper surface of the container that is positioned above the observation area;
    providing a reciprocal movement of the pressing member one or more times so as to push the bubbles outside the observation area, wherein each reciprocal movement comprises moving the pressing member from an upper side of the container to a lower side of the container, moving the pressing member from the lower side to the upper side, and moving the pressing member from the upper side to the lower side: and stopping the pressing member at a position where the pressing member is moved at the lower side.
6. The apparatus for removing bubbles according to claim 5, wherein prior to providing the reciprocal movement,
    the driving unit presses the pressing member at an angle against the part of the upper surface of the container that is positioned above the observation area and moves the pressing member until the pressing member becomes horizontal relative to the upper surface of the container.
7. The apparatus for removing bubbles according to claim 5, wherein prior to providing the reciprocal movement,
    the driving unit presses the pressing member at an angle against the part of the upper surface of the container that is positioned above the observation area and swings the pressing member between a position where the pressing member is held at the angle and a position where the pressing member is horizontal relative to the upper surface of the container.

8. The apparatus for removing bubbles, according to claim 5, further comprising another pressing member and another driving unit wherein
   the another pressing members is a rod-like member, and
   the another driving unit presses horizontally against the upper surface of the container and moves the rod-like member in the horizontal direction so as to pass the rod-like member over the part of the upper surface of the container that is positioned above the observation area.

9. The method for removing bubbles according to claim 1, wherein the container is a culture bag containing a culture liquid.

10. The apparatus for removing bubbles according to claim 5, wherein the container is a culture bag containing a culture liquid.

* * * * *